United States Patent [19]

Costantini et al.

[11] 4,297,287

[45] Oct. 27, 1981

[54] PRODUCTION OF EPOXIDES FROM LOWER ALKANE-1,2-DIOLS

[75] Inventors: Michel Costantini, Lyons; Michel Jouffret, Francheville-le-Bas, both of France

[73] Assignee: Rhone-Poulenc Industries, Paris, France

[21] Appl. No.: 158,317

[22] Filed: Jun. 10, 1980

Related U.S. Application Data

[63] Continuation of Ser. No. 942,361, Sep. 14, 1978, abandoned, which is a continuation-in-part of Ser. No. 889,732, Mar. 24, 1978, abandoned.

[30] Foreign Application Priority Data

Mar. 24, 1977 [FR] France .................................. 77 10140

[51] Int. Cl.$^3$ ............................................. C07D 301/02
[52] U.S. Cl. ................................................ 260/348.16
[58] Field of Search ..................................... 260/348.16

[56] References Cited

U.S. PATENT DOCUMENTS 4,158,008  6/1979  Weitz et al. .................... 260/348.16

FOREIGN PATENT DOCUMENTS 2504981  8/1976  Fed. Rep. of Germany.

OTHER PUBLICATIONS

H. R. Ansari et al., Tetrahedron Letters No. 35 (1975) pp. 3085–3086.
Chemical Abstracts, vol. 81 (1974) 135930w.

Primary Examiner—Norma S. Milestone
Attorney, Agent, or Firm—Burns, Doane, Swecker & Mathis

[57] ABSTRACT

Epoxides, e.g., ethylene and propylene oxides, are prepared from lower alkane-1,2-diols by dehydrating the corresponding diol, in liquid phase, under at least atmospheric pressure, and in the presence of at least one high-boiling organic carboxylic acid and at least one alkali metal or alkaline earth metal carboxylate.

21 Claims, No Drawings

PRODUCTION OF EPOXIDES FROM LOWER ALKANE-1,2-DIOLS

This application is a continuation of application Ser. No. 942,361, filed Sept. 14, 1978, now abandoned, which in turn is a continuation-in-part of application Ser. No. 889,732, filed Mar. 24, 1978 and now abandoned.

BACKGROUND OF THE INVENTION

1. Field of the Invention

The present invention relates to a process for the preparation of epoxides from lower alkane-1,2-diols. More particularly, the invention relates to a process for dehydrating ethylene glycol or propylene glycol to give the corresponding oxide, (i) in the liquid phase, (ii) at a pressure which is equal to or greater than atmospheric, and (iii) in the presence of a least one high-boiling carboxylic acid and at least one alkali metal or alkaline earth metal carboxylate.

2. Description of the Prior Art

It is well known to the art that epoxides such as ethylene oxide or propylene oxide are conventionally prepared via the chlorohydrin route. However, this process has the disadvantage in that it produces polluting effluents.

Methods are also known for preparing epoxides by oxidizing olefins, especially with molecular oxygen or the organic hydroperoxides. However, in the oxidation by means of oxygen, acids are formed, in particular formic acid, which readily react with the epoxides to give undesirable by-products; these secondary reactions occur notably in that stage when the epoxides are separated from the reaction medium. In the oxidation with hydroperoxides, the alcohol which corresponds to the hydroperoxide employed, and the utilization of which is frequently uncertain, is obtained in addition to the desired epoxide.

Methods for producing epoxides have also been described, which consist of decomposing either hydroxyesters of organic acids in the vapor phase (French patent application No. 2,224,454, dated Mar. 8, 1974, and U.S. Pat. No. 4,012,424, both assigned to Chem Systems Inc.), or cyclic esters obtained from alkane-1,2-diols and from compounds such as phosgene or sulfuryl chloride (German patent application No. 1,940,205, dated Aug. 7, 1968, assigned to Farbwerke Hoechst), into epoxides and acids (or anhydrides of inorganic acids).

In the first proposed process, the difficulty lies in the route to the monoacetate, because vicinal hydroxyesters tend to disproportionate into α-glycol and diacetate, at the high temperatures required to carry out the said process.

The second proposed process leads to the consumption of a co-reactant, and the evolution of carbon dioxide gas. Therefore, this process cannot logically be considered for industrial purposes.

In addition, the formation of large amounts of acids poses corrosion problems in both proposed processes.

Furthermore, there is an abundance of literature articles on the subject of dehydration of diols. In general terms, this literature teaches that epoxides or cyclic ethers can be produced by dehydrating diols which contain an aliphatic ring or one or more aromatic nuclei in their molecules, or diols which belong to the wholly aliphatic series and in which the hydroxyl groups are not located on adjacent carbon atoms, but that, on the other hand, in the case of vicinal aliphatic diols, and especially in the case of the 1,2-diols, no epoxides are produced, the dehydration preferentially yielding aldehydes and ketones.

The only pertinent information to be gleaned from the prior art is the formation of propylene oxide as a by-product, in addition to the propionaldehyde obtained as the principal product, during the dehydration of propylene glycol over catalysts based on alumina, silica and copper or nickel oxide [*Chemical Abstracts.* 54, 10,844 g (1960)] and the production of an epoxide by dehydrating cyclodecanediol or another heavy diol, which was, moreover, not completely defined, namely, a 2-alkoxy-2,6-dimethyloctane-7,8-diol, in the presence of m-toluic acid and a trace quantity of sodium acetate. [H. R. Ansari and R. Clark, *Tetrahedron Letters,* No. 35, pages 3,085–3, 3,086 (1975)]. However, according to experiments conducted by the assignee thereof, application of the latter method to propylene glycol does not provide any appreciable amount of propylene oxide.

SUMMARY OF THE INVENTION

It has now unexpectedly been found that the preferential formation of epoxides can readily be accomplished by dehydrating lower alkane-1,2-diols of the aliphatic series, and which process does not exhibit the disadvantages associated with the aforementioned methods for the manufacture of epoxides.

Briefly, the present invention relates to a process for the preparation of the lower alkylene oxides, specifically of ethylene oxide or propylene oxide, comprising contacting the corresponding alkane-1,2-diol with at least one heavy carboxylic acid, in the presence of at least one alkali metal or alkaline earth metal carboxylate, the anion of which can be identical to, or different from, that of the noted acid selected, in the liquid phase, at a pressure which is greater than or equal to atmospheric and at a temperature which is greater than or equal to 200° C.

DETAILED DESCRIPTION OF THE INVENTION

By the expressions "heavy carboxylic acid" there is intended an acid having a boiling point which is higher than that of the diol employed, or if a solvent is used which is more volatile than the diol, an acid having a boiling point which is above that of the solvent, and which acid is sufficiently stable under the reaction conditions. Heavy carboxylic acids which are at least partially soluble in the reaction medium and under the reaction conditions are preferably used.

Aromatic acids or diacids, such as subtituted benzoic acids, o-, m- and p-toluic acids, naphthoic acid, phthalic acids and naphthalenedicarboxylic acids, and aliphatic acids or diacids, such as lauric, stearic, succinic, glutaric and adipic acids, are mentioned as carboxylic acids which can advantageously be used within the scope of the present invention. An aromatic or long-chain aliphatic monoacid is preferably used.

In one prefered embodiment of the present invention toluic or stearic acid is used.

Lithium, sodium, potassium, cesium, calcium and barium carboxylates are mentioned, in particular, as alkali metal or alkaline earth metal carboxylates which can advantageously be used within the scope of the present invention. Mixtures of carboxylates of these various cations can also be used. An alkali metal carboxylate, especially a sodium or potassium carboxylate, is preferably used.

The anion of the alkali metal or alkaline earth metal is preferably derived from a heavy carboxylic acid; said anion can be different from that of the acid employed; however, a carboxylate which corresponds to the acid employed is preferably used. Alkali metal or alkaline earth metal carboxylates which are at least partially soluble in the reaction medium and under the reaction conditions are preferably used.

The relative proportion of carboxylic acid and of carboxylate employed is not critical and can vary over wide limits. Generally, a proportion is employed of between 0.01 and 100 mols of acid per mol of carboxylate, and preferably between 0.05:1 and 30:1.

In another embodiment according to the invention, the alkali metal or alkaline earth metal carboxylate is prepared in situ, by reacting the carboxylic acid employed with the corresponding metal hydroxide.

The process according to the invention is carried out in the liquid phase and the carboxylic acid and alkali metal or alkaline earth metal carboxylate, which are denoted in the text which follows by the expression "catalytic material," are either wholly or partially dissolved in the reaction medium. The catalytic material can therefore be in solution or partially in suspension. When conducting the process according to the invention in the absence of added solvent such as that hereinbelow discussed, sufficient pressure is applied to maintain the reaction medium in the liquid state.

In a preferred embodiment, the reaction is carried out in a solvent for all or a part of the catalytic material.

Solvents which are less volatile than the glycol are preferably used. As examples of suitable solvents for carrying out the invention, there are mentioned: poly(oxyalkylene) glycols, and especially poly(oxyethylene) glycols and poly(oxypropylene) glycols, ethers, such as diphenyl oxide, and ethes of di- or triethylene glycols or of di- or tri-propylene glycols, alkylbenzenes, polyphenyls and, more particularly, bi- and terphenyls.

The reaction is preferably carried out in the presence of terphenyls or others, and, more particularly, in the presence of poly(oxyethylene) glycols.

When the reaction is carried out in the presence of a solvent, the concentration of the alkane-1,2-diol in the reaction medium can vary over wide limits. The reaction is preferably carried out with concentrations on the order of 0.5 to 5 mols of diol per liter in the medium in question.

The amount of catalytic material employed is not critical and it too can vary over wide limits; however, it must not be too high to ensure that the reaction medium remains sufficiently fluid. In principle, a minimum amount of 0.1% by weight of the reaction mixture is required for the catalytic effect to be sufficient. The amount of catalytic material preferably is about 1% by weight of the reaction medium.

The reaction temperature ranges between 200° and 400° C., although these lower and upper limits are not strict limitations. However, if the reaction is carried out below 200° C., the reaction rate becomes too slow, whereas degradation of the reactants and the product are observed at temperatures above 400° C. The reaction is preferably carried out at a temperature ranging between 250° and 350° C.

The reaction can be carried out over a relatively wide pressure range which is between atmospheric pressure and 80 bars, and preferably lower than or equal to 50 bars.

The reaction can be carried out discontinuously or, preferably, continuously in the following manner:

In practice, at least one carboxylic acid and at least one carboxylate, a portion of the alkane-1,2-diol in question, if appropriate, and optionally the solvent in which the reaction can take place, are introduced into a reactor. The mixture is then heated to the desired temperature, while varying the pressure. The remainder of the alkane-1,2-diol selected is then injected continuously.

The epoxide is most preferably continuously removed as soon as it is formed, entraining part of the diol and/or solvent employed. At the outlet of the reactor, the gaseous mixture produced by the reaction is cooled to a suitable temperature, which is on the order of 160° C. and which depends on the particular conditions for effecting the recovery of the condensable products. By continuously removing the product epoxide as soon as it is formed, a good selectivity is assured, since, were the epoxide to be permitted to remain in the reaction mixture for extended periods of time, a portion thereof might be degraded, resulting in the co-production of by-products and, as a consequence thereof, a poorer selectivity. Nonetheless, the aforesaid immediate and continuous product removal remains optional and a most preferred embodiment only, as good yields of epoxide are produced in any event, and whether or not the reaction is conducted in the added presence of the optional inert organic solvent. Specifically referring to said optional solvent, it will be appreciated, and as will later be seen, e.g., in the following Table I, that in the absence of same certain amounts of the ether alcohols are formed, whereas, in conducting the reaction in the presence of such reaction solvent, this by-product formation is limited (Table II). Accordingly, by using the solvent yields of product epoxide are increased and yields of by-product ether alcohols are decreased. Thus, while use of the solvent is strictly optional according to the invention, its actual use marks an especially preferred and technically unexpected and desirable embodiment thereof.

The desired epoxide can in any event be isolated from the condensate by any suitable means, such as distillation, extraction, or the like, and the diol can be recycled.

In order to further illustrate the present invention and the advantages thereof, the following specific examples are given, it being understood that same are intended only as illustrative and in nowise limitative.

EXAMPLES 1 to 8

About 4 mols (304 g) of propane-1,2-diol and the catalytic material, namely, p-toluic acid and sodium hydroxide which had first been homogenized, were introduced into a pressure distillation apparatus. The mixture was then heated to the desired temperature ($\theta$), while varying the pressure. When this temperature had been reached, 4 mols of propane-1,2-diol were continuously injected over the course of 2 hours 20 minutes and the distillate was simultaneously continuously drawn off, the rate of withdrawal being equal to the feed rate. A distillate was collected which comprised unconverted propane-1,2-diol and the volatile materials formed.

The particular conditions and the results obtained are given in the following Table 1, in which DC is the degree of conversion of the propane-1,2-diol S(PO) is the selectivity with respect to propylene oxide relative to the volatile materials, Y(PO) is the yield of propylene oxide and Y(EA) is the yield of ether alcohol (mixture of dipropylene glycols).

mixture of o-, m- and p-terphenyls, in which the m-isomer is preponderant.

TABLE II

| No of Example | Solvent | REACTANTS IN MOL/LITER | | | | CONDITIONS | | | RESULTS (%) | | | |
|---|---|---|---|---|---|---|---|---|---|---|---|---|
| | | Propane 1,2-Diol | ACID | | SALT | | P | RT | | | | |
| | | | Nature | Concentration | Nature* | Concentration | θ° C. | (bar) | (minutes) | DC | S(PO) | Y(PO) | Y(EA) |
| 9 | PEG 1500 | 2.28 | p-tol | 0.110 | Li | 0.110 | 282 | 1.8 | 31 | 14.0 | 60.2 | 53.4 | 6.6 |
| 10 | PEG 1500 | 2.49 | p-tol | 0.108 | Na | 0.108 | 284 | 2.3 | 35 | 7.6 | 87.3 | 76.9 | 11.1 |
| 11 | PEG 1500 | 2.49 | p-tol | 0.108 | K | 0.108 | 284 | 2 | 35 | 6.8 | 92.3 | 81.5 | 11.7 |
| 12 | PEG 1500 | 2.46 | p-tol | 0.108 | Cs | 0.108 | 283 | 1.8 | 34 | 7.5 | 90.8 | 74.4 | 18.0 |
| 13 | PEG 1500 | 2.34 | p-tol | 0.110 | Ca | 0.055 | 285 | 2.2 | 32 | 2.9 | 51.2 | 45.8 | 5.9 |
| 14 | PEG 1500 | 2.40 | p-tol | 0.109 | Ba | 0.0545 | 285 | 2.2 | 33 | 1.4 | 89.2 | 80.5 | 9.0 |
| 15 | PEG 1500 | 2.40 | adipic | 0.054 | sodium adipate | 0.109 | 285 | 1.8 | 33 | 1.0 | 93.8 | 56.1 | 38.9 |
| 16 | PEG 1500 | 2.63 | succinic | 0.053 | sodium succinate | 0.107 | 284 | 1.9 | 37 | 2.0 | 93.6 | 61.4 | 34.4 |
| 17 | PEG 1500 | 2.49 | p-tol | 0.108 | sodium stearate | 0.108 | 285 | 1.7 | 35 | 10.3 | 90.4 | 73.1 | 18.6 |
| 18 | PEG 1500 | 4.2 | p-tol | 0.095 | Na | 0.095 | 282 | 4.7 | 70 | 10.3 | 88.9 | 65.3 | 25.3 |
| 19 | benzophenone | 2.20 | p-tol | 0.111 | Na | 0.111 | 285 | 2.0 | 40 | 4.6 | 79.6 | 68.9 | 5.9 |
| 20 | $\phi_2O$ | 3.76 | p-tol | 0.095 | Na | 0.095 | 284 | 5.3 | 60 | 13.3 | 84.5 | 71.0 | 14.8 |
| 21 | $\phi_2O$ | 3.76 | stearic | 0.095 | sodium stearate | 0.095 | 284 | 5.5 | 60 | 18.7 | 88.6 | 64.9 | 25.0 |
| 22 | OM2 | 2.28 | stearic | 0.110 | sodium stearate | 0.110 | 280 | 2.7 | 31 | 14.3 | 81.5 | 63.2 | 18.5 |

*p-toluate, unless otherwise indicated.

TABLE I

| NO of EXAMPLE | CATALYSTS Concentration in mol/liter | | | | RESULTS IN % | | | |
|---|---|---|---|---|---|---|---|---|
| | Acid | Salt | Acid +Salt | Acid/ Salt | 0° C. | DC | S(PO) | Y(PO) | Y(EA) |
| 1 | 0.068 | 0.682 | 0.750 | 0.1 | 220 | 3.5 | 96.2 | 49.9 | 48.1 |
| 2 | 0.068 | 0.682 | 0.750 | 0.1 | 246 | 16.8 | 90.1 | 21.9 | 75.2 |
| 3 | 0.068 | 0.682 | 0.750 | 0.1 | 286 | 41.2 | 72.6 | 17.8 | 71.6 |
| 4 | 0.020 | 0.662 | 0.682 | 0.03 | 286 | 35.8 | 66.4 | 14.7 | 72.4 |
| 5 | 0.029 | 0.026 | 0.055 | 1.1 | 282 | 6.2 | 87.2 | 26.1 | 70.1 |
| 6 | 0.087 | 0.136 | 0.223 | 0.64 | 282 | 24.5 | 82.0 | 27.7 | 65.1 |
| 7 | 0.433 | 0.682 | 1.115 | 0.63 | 277 | 29.0 | 71.4 | 29.1 | 56.5 |
| 8 | 0.682 | 0.068 | 0.750 | 10.0 | 285 | 11.6 | 78.5 | 43.5 | 43.1 |

EXAMPLES 9 to 22

The solvent, the catalytic material, namely, the acid and the metal hydroxide in question which had first been homogenized, and, optionally, a certain amount of propane-1,2-diol were introduced into a pressure distillation apparatus; the mixture was then heated to the desired temperature (θ), while varying the pressure. 1.64 mols/hour of propane-1,2-diol were continuously injected and the distillate was simultaneously drawn off, the rate of withdrawal being equal to the feed rate. A distillate was collected which comprised unconverted propane-1,2-diol and the volatile materials formed. The duration of the experiments was about 2 hours 20 minutes. The particular conditions and the results obtained are given in Table II, in which the concentration of the reactants is given in mol/liter in the steady state with respect to the propane-1,2-diol, RT denotes the residence time of the propane-1,2-diol, P denotes the pressure in bars, $\phi_2O$ denotes diphenyl oxide, PEG 1,500 denotes a poly(oxyethylene) glycol having a number average molecular weight on the order of 1,500, p-tol denotes p-toluic acid and OM2 denotes a commercial

EXAMPLE 23

The reaction was carried out in accordance with the general method described for Examples 9 to 22, but using ethylene glcyol and a poly(oxyethylene)glycol having a number-average molecular weight on the order of 1,500 as the charge.

The conditions were as follows:
Concentration of p-toluic acid: 0.11 mol/liter
Concentration of sodium p-toluate: 0.11 mol/liter
Concentration of ethylene glycol in the stationary state: 2.69 mols/liter
Temperature: 280° C.
Pressure: 2.2 bars
Injection rate: 2.15 mols/hour of ethylene glycol
Duration of the experiment: 2 hours 20 minutes
The results obtained were as follows:
Degree of conversion of the diol: 8.5%
Selectivity with respect to ethylene oxide relative to the volatile materials: 95%.
Yield of ethylene oxide: 52.4%

EXAMPLE 24 (a-b-c)

Comparison experiments on propane-1,2-diol

The general conditions were those of Examples 1 to 8. The particular conditions and results are given in the following Table III.

TABLE III

| EXAMPLE | CATALYST | | | | θ° C. | RESULT % | | | |
|---|---|---|---|---|---|---|---|---|---|
| | Acid | | Salt | | | | | | |
| | Nature | Concentration mol/liter | Nature | Concentration mol/liter | | DC | S(PO) | Y(PO) | Y(EA) |
| 24 - a | | 0 | | 0 | 283 | 0.3 | 70.8 | 8.7 | 87.7 |
| 24 - b | | 0 | sodium toluate | 0.682 | 287 | 36.8 | 73.5 | 15.1 | 75.8 |
| 24 - c | p-tol | 0.682 | | 0 | 285 | 3.5 | 37.8 | 14.5 | 50.9 |

Comparison experiment 24-a shows that thermal dehydration alone leads essentially to the production of heavy products, despite a very low conversion.

Comparison experiment 24-b shows that dehydration in the presence of the carboxylate alone leads essentially to the production of heavy products, with the high conversion ratio of the glycol.

Comparison experiment 24-c shows that, although dehydration in the presence of the carboxylic acid alone leads to the production of propylene oxide, only a very poor selectivity relative to the volatile materials is achieved.

While the invention has now been described in terms of various preferred embodiments and illustrated with respect to certain examples, it will be apparent to the skilled artisan that various omissions, substitutions, modifications and the like may be made without departing from the spirit of the invention. Accordingly, it is intended that the scope of the present invention be limited only by the following claims.

What is claimed is:

1. A process for the preparation of a lower alkylene oxide, which comprises dehydrating a lower alkane-1,2-diol selected from the group consisting of ethylene glycol and propylene glycol, in liquid phase, under a pressure of at least atmospheric, at a temperature of from 200° to 400° C., and in the presence of a mixture comprising at least one heavy carboxylic acid and at least one alkali metal or alkaline earth metal carboxylate, wherein the amount of heavy carboxylic acid present per mole of carboxylate ranges from 0.01 to 100 mols and the concentration of the heavy carboxylic acid/carboxylate admixture in the reaction mixture being at least 0.1% by weight, wherein the dehydration is conducted in the presence of a solvent for the heavy carboxylic acid/carboxylate admixture, selected from the group consisting of poly (oxyalkylene) glycols, ethers, alkylbenzenes and polyphenyls, and wherein the product epoxide is continuously removed as it is formed.

2. The process as defined by claim 1, wherein the solvent is selected from the group consisting of poly(oxyethylene) glycol, poly(oxypropylene) glycol, diphenyl oxide, ethers of di- or triethylene glycol, ethers of di- or tripropylene glycol, biphenyl and terphenyls.

3. The process as defined by claim 2, wherein the solvent is a terphenyl.

4. The process as defined by claim 2, wherein the solvent is poly(oxyethylene) glycol.

5. The process as defined by claim 1, wherein the concentration of diol in the reaction mixture ranges from between 0.5 to 5 mols per liter.

6. The process as defined by claim 1, wherein the amount of heavy carboxylic acid present per mol of carboxylate ranges from between 0.05 and 30 mols.

7. The process as defined by claim 1, wherein the heavy carboxylic acid is selected from the group consisting of an organic aromatic carboxylic acid and an organic aliphatic carboxylic acid.

8. The process as defined by claim 7, wherein the heavy carboxylic acid is an aromatic monoacid.

9. The process as defined by claim 7, wherein the heavy carboxylic acid is a long-chain aliphatic monoacid.

10. The process as defined by claim 7, wherein the heavy carboxylic acid is a dicarboxylic acid.

11. The process as defined by claim 7, wherein the heavy carboxylic acid is selected from the group consisting of substituted benzoic acids, o-, m- and p-toluic acids, naphthoic acid, phthalic acids, naphthalenedicarboxylic acids, lauric acid, stearic acid, succinic acid, glutaric acid and adipic acid.

12. The process as defined by claim 11, wherein the heavy carboxylic acid is a toluic acid.

13. The process as defined by claim 11, wherein the heavy carboxylic acid is stearic acid.

14. The process as defined by claim 1, wherein the cation of the carboxylate is selected from the group consisting of lithium, sodium, potassium, cesium, calcium and barium.

15. The process as defined by claim 14, wherein the cation is selected from the group consisting of sodium and potassium.

16. The process as defined by claim 14, wherein the carboxylate is of the heavy carboxylic acid present.

17. The process as defined by claim 1, wherein the dehydration is conducted at a temperature of from 250° to 350° C.

18. The process as defined by claim 1, wherein the dehydration is conducted under a pressure of from atmospheric to 80 bars.

19. The process as defined by claim 18, wherein the dehydration is conducted under a pressure of no greater than 50 bars.

20. The process as defined by claim 1, further comprising recovering the product epoxide.

21. The process as defined by claim 20, further comprising recycling untreated diol.

* * * * *